(12) United States Patent
Draget et al.

(10) Patent No.: US 8,529,890 B2
(45) Date of Patent: Sep. 10, 2013

(54) COMPOSITION FOR THE ADMINISTRATION OF POLYMERIC DRUGS

(75) Inventors: Kurt Ingar Draget, Trondheim (NO); Catherine Taylor, Trondheim (NO)

(73) Assignee: NTNU Technology Transfer AS, Trondheim (NO)

( * ) Notice: Subject to any disclaimer, the term of this patent is extended or adjusted under 35 U.S.C. 154(b) by 0 days.

(21) Appl. No.: 13/259,116

(22) PCT Filed: Mar. 23, 2010

(86) PCT No.: PCT/GB2010/000538
§ 371 (c)(1),
(2), (4) Date: Dec. 7, 2011

(87) PCT Pub. No.: WO2010/109180
PCT Pub. Date: Sep. 30, 2010

(65) Prior Publication Data
US 2012/0100210 A1   Apr. 26, 2012

(30) Foreign Application Priority Data

Mar. 23, 2009 (GB) .................................. 0904942.0

(51) Int. Cl.
*A61K 9/28* (2006.01)
*A61K 9/16* (2006.01)
*A61K 9/00* (2006.01)

(52) U.S. Cl.
CPC ....................................... *A61K 9/28* (2013.01)
USPC ....................................... 424/94.61; 514/460

(58) Field of Classification Search
None
See application file for complete search history.

(56) References Cited

U.S. PATENT DOCUMENTS

| | | | |
|---|---|---|---|
| 4,225,592 A | 9/1980 | Lakatos et al. | |
| 5,166,137 A | 11/1992 | Otterlei et al. | |
| 5,459,054 A | 10/1995 | Skjak-Braek et al. | |
| 5,460,957 A | 10/1995 | Hiura et al. | |
| 5,683,991 A | 11/1997 | Guggenbichler et al. | |
| 5,759,572 A | 6/1998 | Sugimoto et al. | |
| 5,795,587 A | 8/1998 | Gao et al. | |
| 6,121,441 A | 9/2000 | Simensen et al. | |
| 6,339,075 B1 | 1/2002 | King et al. | |
| 6,407,226 B1 | 6/2002 | Simensen et al. | |
| 6,440,413 B1 | 8/2002 | Hooreman | |
| 6,747,015 B2 | 6/2004 | Byon et al. | |
| 2003/0013678 A1 | 1/2003 | Lang et al. | |
| 2003/0022863 A1 | 1/2003 | Stahl et al. | |
| 2003/0059474 A1 | 3/2003 | Scott et al. | |
| 2003/0224070 A1 | 12/2003 | Sweazy et al. | |
| 2004/0073964 A1 | 4/2004 | Ellington et al. | |
| 2004/0224922 A1 | 11/2004 | King | |
| 2005/0158392 A1 | 7/2005 | Kim et al. | |
| 2006/0083780 A1 | 4/2006 | Heyes et al. | |
| 2009/0010914 A1 * | 1/2009 | Taylor et al. ............... | 424/94.61 |

FOREIGN PATENT DOCUMENTS

| | | | |
|---|---|---|---|
| CA | 2 428 473 | A1 | 5/2002 |
| DE | 268865 | A1 | 6/1989 |
| DE | 19520743 | A1 | 12/1996 |
| EP | 324720 | A1 | 7/1989 |
| EP | 506325 | A1 | 9/1992 |
| EP | 0888778 | A1 | 1/1999 |
| EP | 1234584 | | 8/2002 |
| EP | 1714660 | A1 | 10/2006 |
| EP | 1745705 | A1 | 1/2007 |
| EP | 1837018 | A1 | 9/2007 |
| FR | 7576 | M | 1/1970 |
| GB | 1042379 | | 9/1966 |
| GB | 2 430 881 | A1 | 4/2007 |
| JP | 61-076413 | | 4/1986 |
| JP | 01-197431 | | 8/1989 |
| JP | 09208472 | A | 8/1997 |
| JP | 2000-034302 | | 2/2000 |
| JP | 2002-338493 | A | 11/2002 |
| JP | 2005-145885 | | 6/2005 |
| JP | 2006-028041 | | 2/2006 |
| WO | WO 88/09794 | A1 | 12/1988 |
| WO | WO 91/07951 | A1 | 6/1991 |
| WO | WO 91/11205 | A1 | 8/1991 |
| WO | WO 95/18145 | A1 | 7/1995 |
| WO | WO 98/13024 | A2 | 4/1998 |
| WO | WO 01/15672 | A2 | 3/2001 |
| WO | WO 01/17506 | A1 | 3/2001 |
| WO | WO 01/66084 | A2 | 9/2001 |
| WO | WO 01/72278 | A2 | 10/2001 |
| WO | WO 2005/089722 | A1 | 9/2005 |
| WO | WO 2007/002224 | A2 | 1/2007 |
| WO | WO 2007/039754 | A1 | 4/2007 |
| WO | WO 2007/039760 | A1 | 4/2007 |

(Continued)

OTHER PUBLICATIONS

Arno Hanninen and Leonard C. Harrsion, Mucosal Tolerance to Prevent Type 1 Diabetes: Can the Outcome Be Improved in Humans?, 2004, Rev Diabetic Stud, 1:113-121.*
Merck Manual, Disorders, http://www.merckmanuals.com/professional/index.html, accessed Aug. 6, 2012.*
Merck Manual, Diseases, http://www.merckmanuals.com/professional/index.html, accessed Aug. 6, 2012.*
Merck Manual, Diabetes, http://www.merckmanuals.com/professional/index.html, accessed Aug. 6, 2012.*
Aikiyama, Hisayoshi et al. (1991) "Effect of Depolymerized Alginates on the Growth of Bifidobacteria" *Biosci. Biotech. Biochem* 56: 355-356.

(Continued)

*Primary Examiner* — Jean C. Witz
*Assistant Examiner* — Mindy Newman
(74) *Attorney, Agent, or Firm* — Knobbe, Martens, Olson & Bear, LLP (57) ABSTRACT

Provided are improvements in and relating to pharmaceutical compositions for oral administration of polymeric biological drug substances and to methods of treatment using such compositions. In particular, an oral and/or mucosal pharmaceutical composition is provided, said composition comprising an enteric-coated drug substance, and also comprising an enteric-coated oligouronate, wherein said drug substance is a polymeric biological drug substance.

11 Claims, 12 Drawing Sheets

(56) References Cited

FOREIGN PATENT DOCUMENTS

| WO | WO 2007/046719 A2 | | 4/2007 |
|---|---|---|---|
| WO | WO 2008/125828 A2 | * | 10/2008 |
| WO | WO 2008/137114 A1 | | 11/2008 |
| WO | WO 2009/142892 A2 | | 11/2009 |

OTHER PUBLICATIONS

Banning D. et al. 1997 "Oscillatory and thermorheological characterization of alginate/mucin mixes" Pharmacy and Pharmacology (British Pharmaceutical Conference 1997 Science proceedings 134$^{th}$ meeting, Scarborough, Sep. 15-18, 1997, Abstract 65.

Chono, S. et al. 2008 "An efficient and low immunostimulatory nanoparticle formulation for systemic siRNA delivery to the tumor" *Journal of Controlled Release* 131: 64-69.

Dalby, B. et al. 2004 "Advanced transfection with Lipofectamine 2000 reagent: primary neurons, siRNA, and high-throughput applications" *Methods* 33: 95-103.

Eiselt, Petra et al. (2000) "Porous carriers for biomedical applications based on alginate hydrogels" *Biomaterials* 21: 1921-1927.

Fiel, Stanley B. et al. (1995) "Comparison of Three Jet Nebulizer Aerosol Delivery Systems Used to Administer Recombinant Human DNase I to Patients With Cystic Fibrosis" *Chest Official Publication of the American College of chest Physicians* 108: 153-156.

Jiang, G. et al. 2007 "DNA/PEI/Alginate polyplex as an efficient in vivo gene delivery system" *Biotechnology and Bioprocessing Engineering* 12: 684-689.

Murata, K. et al. 1992 "Continuous depolymerization of alginates by a non-support bioreactor system containing flocculated bacterial cells" *Journal of Fermentation and Bioengineering* 73:172-174.

Klöck, G. et al. 1997 "Biocompatibility of mannuronic acid-rich alginates" *Biomaterials* 18: 707-713.

Kong, H. J. et al. 2008 "Design of Biodegradable Hydrogel for the Local and Sustained Delivery of Angiogenic Plasmid DNA" *Pharaceutical Research* 25: 1230-1238.

Krebs, M. D. et al. 2009 "Localized and Sustained Delivery of Silencing RNA from Macroscope Biopolymer Hydrogels" *Journal of the American Chemical Society* 131: 9204-9206.

Pandey, Rajesh & Khuller, G.K. (2005) "Chapter 27: Alginate as a Drug Delivery Carrier" *Handbook of Carbohydrate Engineering* pp. 799-815.

Rakkhithawatthana, V. et al. 2010 "Investigation of gene transferring efficacy through nano-polyplex consisting of methylated N-(4-pyridinylmethyl) chitosan chloride and poly(ethylenimine) in human cell lines" *Carbohydrate Polymers* 80: 276-284.

Sioud, M. et al. 2003 "Cationic liposome-mediated delivery of siRNAS in adult mice" *Biochemical and Biophysical Research Communications* 312: 1220-1225.

Tadashi, Yoshimatsu et al. (2002) "Effects on Intestinal Flora of a Beverage Containing Non-fermentable Depolymerized Sodium Alginate and Water-soluable Fermentable Corn Bran Fiber" *The Journal of Nutrition and Dietetics* 60: 137-143.

Tang, J.X. et al. 2005 "Anionic poly(amino acid)s dissolve F-actin and DNA bundles, enhance DNase activity, and reduce the viscosity of cystic fibrosis sputum" *Am J Physiol Lung Cell Mol Physiol* 289: L599-L605.

Terada, A. et al. (1995) "Effect of Dietary Alginate on the Faecal Microbiota and Faecal Metabolic Activity in Humans" *Microbial Ecology in Health and Disease* 8: 259-266.

Yun, Y. H. et al. 2004 "Hyaluronan microspheres for sustained gene delivery and site-specific targeting" *Biomaterials* 25: 147-157.

Westedt, U. et al. 2007 "Poly(vinylalcohol)-graft-poly(lactide-co-glycolide) nanoparticles for local delivery of paclitaxel for restenosis treatment" *Journal of Controlled Release* 119: 41-51.

Grasdalen, H. et al. 1979 "A.P.M.R. study of the composition and sequence of urinate residues in alginates" *Carbohydrate Research* 68: 23-31.

Iwamoto, M. et al. 2005 "Structure—activity relationship of alginate oligosaccharides in the induction of cytokine production from RAW264.7 cells" *FEBS Letters* 579: 4423-4429.

Witschi, C. et al. 1999 "In vitro evaluation of microparticles and polymer gels for use as nasal platforms for protein delivery" *Pharmaceutical Research* 16: 382-390.

\* cited by examiner

COMPOSITION FOR THE ADMINISTRATION OF POLYMERIC DRUGS

This invention relates to improvements in and relating to pharmaceutical compositions for oral administration of polymeric biological drug substances and to methods of treatment using such compositions.

Patient acceptance of drug treatment, and the ease of drug administration, are significantly higher when the drug substance can be administered orally than when, for example, it has to be injected. Accordingly, the majority of pharmaceutical compositions supplied commercially are formulated for oral administration, e.g. as tablets, capsules or in liquid form.

Oral administration, however, is not always feasible or straightforward, for example where the drug substance is unstable in gastric fluid and so fails to reach the intestines where it may be taken up from the gut. The conventional approach to instability to gastric juice has been to administer such drug substances in tablet, capsule or dispersion form, with the tablets, capsules or particles being provided with an enteric coating, i.e. a coating of a material which is insoluble in the stomach but breaks down lower down the gut to release the drug substance it has been used to encapsulate. Enteric coating materials are well known and widely available commercially. Nevertheless, even though the provision of such release-delaying coatings is well established technology, polymeric biological drug substances, e.g. hormones and other peptides, have yet to be successfully formulated for oral administration.

There is thus a continuing need for pharmaceutical dosage forms suitable for the oral administration of polymeric biological drug substances.

We have now found that this need is addressed by the inclusion with the polymeric biological drug substance in an enteric coated oral administration form of an oligouronate, that is a linear oligosaccharide consisting majoritatively of uronate monomer residues. The invention is predicated, in part, on the surprising finding that the penetrability of intestinal mucus is dramatically increased by oligouronates. This finding has enabled the development of drug formulations for oral administration of polymeric drugs, macromolecular drugs in particular, as claimed herein which take advantage of this newly-discovered effect of oligouronates.

For certain treatments, drug substances may be administered mucosally, i.e. brought into contact with a mucosal surface of the human or animal body, e.g. a surface within the gastrointestinal surface, the airway or the vagina. In the case of fish, the mucosal surface may be the skin and vaccines may be administered mucosally to fish, such as salmon, by topical application to the skin or application into the surrounding water. The compositions of the invention are suitable for mucosal application and the invention is claimed accordingly. Oral compositions and administration however are preferred.

Thus viewed from one aspect the invention provides an oral and/or mucosal pharmaceutical composition comprising an enteric-coated drug substance, wherein said composition also comprises an enteric-coated oligouronate and wherein said drug substance is a polymeric biological drug substance.

Viewed from a further aspect the invention also provides a method of treatment of a human or non-human (e.g. avian, reptilian, piscine, or preferably mammalian) subject, which method comprises orally or mucosally administering to said subject an effective dose of a drug substance to combat a condition responsive to said drug substance, the improvement comprising administering said drug substance in the form of a composition according to the invention.

Viewed from another aspect the invention provides the use of an oligouronate for the manufacture of a pharmaceutical composition according to the invention or use in a method of treatment according to the invention.

The compositions of the invention may be in any orally or mucosally administrable form in which the polymeric biological drug substance and the oligouronate are allowed to transit the stomach and be released at the same section of the subsequent parts of the gastrointestinal tract at the same time. Thus the dosage form may be a dispersion, tablet, capsule, chewable gel, etc. Preferably, however, the composition will take the form of a tablet or capsule, coated as a single unit with the enteric, i.e. gastric-juice resistant, coating and/or containing smaller particles provided with such coatings. Preferably, the oligouronate and the polymeric biological drug substance are provided with the same coating(s) as, while not wishing to be bound by theory, it is thought that the oligouronate serves to promote bio-uptake of the polymeric biological drug substance by modifying the permeability of the mucus layer on the lumen of the gut in such a way that the polymeric drug is more able to pass through and reach the surfaces of the cells at the gut lumen. It is also postulated that the bioavailability and uptake of the polymeric drug will be affected synergistically by co-administration with a oligouronate in an enteric coated formulation. In particular, where the oligouronate and drug are released substantially simultaneously, the level of oligouronate is expected to lead to an advantageously increased bioavailability and uptake of the drug.

The material used for the enteric coating may, for example, be any of the materials conventionally used to delay release of drug substances until after the composition has passed out of the stomach. Examples include synthetic and semi-synthetic polymers, such as cellulose acetate phthalate and those available under the trade name Eudragit. The coating should be insoluble in the stomach and should prevent passage of gastric juice components, such as acids, that may break down the polymeric biological drug substance. Such coatings may be applied in conventional fashion and in conventional thicknesses/amounts. If desired, a buffer may be included with the biological drug substance, or within a coating layer, to protect the drug substance still further from any possible leakage of acid before stomach transit is complete.

The polymeric biological drug substance in the compositions of the invention may be any material which is susceptible to breakdown by gastric fluids, which is a polymer of biological origin, or is an analog or derivative of a polymer of biological origin, which has a desired physiological activity as a drug substance (rather than simply as a nutrient for example), and is not an oligosaccharide. The molecular weight of the drug substance will preferably be 500 to 500 k Da, particularly 1 to 50 kDa, especially 3 to 25 kDa. Typically, the biological drug substance will be a peptide, e.g. an oligopeptide or polypeptide, for example a protein or protein fragment, and in particular a hormone. The polymer may be a derivative, e.g. a salt, ester, amide, complex or conjugate. Such derivatives are considered still to be polymeric biological drug substances as their pharmacophore, i.e. the component responsible for the desired physiological activity, remains the polymeric biological component. Particularly preferred hormones/proteins/peptides include: insulin; anti-tumour necrosis factor (anti-TNF); interferons; coagulation factors (e.g. factor VII, factor VIII and factor IX); follicle-stimulating hormones (FSH); erythropoietin; human beta-glucoserobidase; and anti-cancer agents such as: granulocyte-colony stimulating factor (G-CSF); HERCEPTIN; and anti-CD20.

Further preferred drug substances include antigens for oral or mucosal vaccination, e.g. protein fragments from parasitic or infective species optionally conjugated to an immunogenic carrier. Such species may for example be bacteria, viruses, yeasts or fungi. The vaccines may be used for human vaccination; however they are particularly preferred for administration to farmed animals, in particular fish and shellfish, e.g. salmon, trout, cod and prawn.

Most of these polymeric biological drug substances are available commercially, either generically or under trade names such as: ENBREL (generic name, Etanercept), REMICADE (generic name, Infliximab), HUMIRA (generic name, Adalimumab), AVONEX (generic name, interferon β-1a), REBIF (generic name, interferon β-1a), BETASERON (generic name, interferon β-1b), PEGASYS (generic name, pegylated interferon α-2a), PROCRIT (generic name, Epoetin alpha), EPOGEN (generic name, Epoetin alpha), RECONORM (generic name, Epoetin beta), EPOGIN (generic name, Epoetin beta), EPOMAX (generic name, Epoetin alpha), EPREX (generic name, Epoetin alpha), HERCEPTIN (generic name, trastuzumab), RITUXAN (generic name, Rituximab), NEPOGEN (generic name, Filgrastim), NEULASTA (generic name, Pegfilgrastim), and CEREZYME (generic name, Imiglucerase). The conditions they are used to treat cover a wide range, e.g. diabetes, cancer, cardiovascular disease, infertility, and Gaucher's disease.

The dosage of the polymeric biological in the compositions of the invention will typically be in the range of 5 to 100%, especially 10 to 60%, more particularly 20 to 50% of the desired daily dose per dosage unit (or per prescribed dosage volume for a composition not in dosage unit form, e.g. a liquid dispersion). The desired daily dose will generally be from 1 to 10 times, for example 2 to 6 times, the daily dose taken by injection, i.e. the dosages readily determinable from current product data sheets. The ratio between known injection dosage and oral dosage according to the invention may be determined by conventional experimentation, e.g. following determination of the percentage uptake of a labelled analog taken orally and by injection in an animal model. In general, the oral dose may be expected to be 500 to 2,000%, e.g. about 1,000%, of the dose normally given by injection (i.e. a dose 5 to 20-fold, especially about 10-fold the normal injection dose). The particular dosage of course will also depend, as with known administration by injection, on the species and size of the recipient, on the nature and severity of the condition being treated, and on the specific biological drug substance itself.

The oligouronate, as mentioned above, is preferably coated with a release-delaying coating in the same way as, or, more preferably, together with, the polymeric biological drug substance. This is in order to ensure that both the oligouronate and the polymeric biological drug substance are released at substantially the same place and time. Since the function of the oligouronate is thought to be largely to modify the mucosal surface of the gastrointestinal tract, the dose will preferably be higher, in mole terms, than that of the polymeric biological drug substance but need not be a function of the drug substance dose. The oligouronate dose will preferably be 10 to 1,200 mg, especially 50 to 1,000 mg, particularly 100 to 750 mg, per dose unit. While pre-treatment of the gastrointestinal tract with the oligouronate, i.e. sequential administration of oligouronate followed by polymeric biological drug substance, might be thought to be equivalent to simultaneous administration, it is thought that simultaneous administration is preferable since the potentiated uptake is then more closely limited to the desired polymeric biological drug substance.

The counter-ions for the oligouronate may be any of the physiologically tolerable ions commonly used for charged drug substances, e.g. sodium, potassium, ammonium, chloride, mesylate, meglumine, etc. Ions which promote alginate gelation, e.g. group 2 metals, however will preferably not be used. Such group 2 ions will desirably also be essentially absent from the other components of the compositions of the invention.

While the oligouronate, which is linear, may be a synthetic material, it is preferably a derivative, having a weight average molecular weight of less than 100,000 Da, of a naturally occurring polysaccharide. It is preferably a 3- to 28-mer, in particular a 4- to 25-mer, especially a 6- to 22-mer, in particular an 8- to 15-mer, especially a 10-mer, e.g. having a molecular weight in the range 350 to 6,000 Da especially 750 to 4,500 Da. It may be a single compound or it may be a mixture of oligouronates, e.g. of a range of degrees of polymerization. Moreover, the monomeric residues in the oligouronate, i.e. the monosaccharide groups, may be the same or different.

Oligouronates are readily accessible from natural sources since many natural polysaccharides contain uronic acid residues such as guluronic and galacturonic acid residues.

Polysaccharide to oligosaccharide cleavage to produce oligouronates useable according to the present invention may be performed using conventional polysaccharide lysis techniques such as enzymatic digestion and acid hydrolysis. Oligouronates may then be separated from the polysaccharide breakdown products chromatographically using an ion exchange resin or by fractionated precipitation or solubilization.

Examples of polysaccharides containing uronates include naturally occurring polysaccharides (such as xanthan, pectin, alginates, hyaluronan, heparin and chondroitin sulphate) and chemically modified polysaccharides, including but not limited to polysaccharides modified to add charged groups (such as carboxylated or carboxymethylated glycans), and polysaccharides modified to alter flexibility (e.g. by periodate oxidation). Suitable polysaccharides are discussed for example in "Handbook of Hydrocolloids", Ed. Phillips and Williams, CRC, Boca Raton, Fla., USA, 2000. The use of alginates however is especially preferred as these naturally occur as block copolymers of manuronic (M) and guluronic (G) acids and G-block oligomers can readily be produced from alginate source materials. Indeed, in general the oligouronate is preferably an oligoguluronic acid, or less preferably an oligogalacturonic acid.

Where alginates are used as the starting material for preparation of the oligouronate, the guluronic acid content may if desired be increased by epimerization with mannouronan C-5 epimerases from *A. vinelandii*.

Oligoguluronic acids suitable for use according to the invention may conveniently be produced by acid hydrolysis of alginic acid from *Laminaria hyperborea*, dissolution at neutral pH, addition of mineral acid to reduce the pH to 3.4 to precipitate the oligoguluronic acid, washing with weak acid, resuspension at neutral pH and freeze drying.

The use of oligouronates of the type described in WO2008/125828, the contents of which are hereby incorporated by reference, is especially preferred.

The composition of the invention may be produced and administered in conventional fashion. Besides the enteric coating material, the oligouronate and the polymeric biological drug substance, the compositions may contain other conventional pharmaceutical carriers and excipients, e.g. solvents, diluents, buffers, viscosity modifiers, colours, antioxidants, etc.

Particularly where the compositions are for administration to farmed animals, they may be in the form of a feed composition containing the enteric-coated substances, e.g. feed pellets. Such compositions may be prepared by including the enteric-coated substances with the other components of the feed or the enteric-coated substances may be absorbed into pre-prepared feed. This may be done for example in the manner disclosed in WO02/28199 using a dispersion of enteric-coated particles in the water used to soak the feed pellets.

Where antigens are to be administered mucosally, the inclusion of an enteric coating may if desired be dispensed with; nonetheless, such treatment and compositions suitable for use therefor form aspects of the invention. Thus, viewed from one aspect the invention provides a mucosal vaccine composition comprising an antigen, especially a peptidic antigen, and a physiologically tolerable oligouronate, optionally together with a tolerable carrier or excipient. Viewed from a further aspect the invention provides a mucosal vaccine kit comprising an antigen, and, enclosed separately, an oligouronate. Viewed from a still further aspect the invention provides a method of mucosal vaccination of an animal, especially a fish, which method comprises exposing a mucosal surface of said animal simultaneously or sequentially to an effective amount of an antigen, especially a water-soluble antigen, and an effective amount of an oligouronate.

The invention will now be described further with reference to the following non-limiting Figures and Examples, in which.

EXAMPLE 1

Insulin Tablets

The following are mixed thoroughly and pressed to form tablet cores:

| | |
|---|---|
| Talc | 350 mg/tablet |
| Magnesium stearate | 350 mg/tablet |
| Insulin* | 100 Units |
| Sodium guluronate** | 300 mg/tablet |

*available from Alfa Chem, Kings Point, NY, US.
**G-block polymer, DP10, prepared as described in WO2008/125828.

The tablets cores are coated in conventional fashion with an enteric coating agent, e.g. Eudragit® FS30D, available from Evonik Industries AG, Essen, Germany.

EXAMPLE 2

Microbead Uptake in Cells with Mucus Layer

The ability of mucus-secreting HT29-MTX cells to take up microbeads was assessed. Cells having a discontinuous mucus layer and cells having a continuous mucus layer were investigated as follows.

HT29-MTX cells (*Clin. Otolaryngol. Allied Sci.* (2003) 28(1):p. 39-42) were grown to confluence in 24 well plates. Dulbecco's Modified Eagle Medium, DMEM (GIBCO) was used. For wells designated confluent, mucus layer cells were grown under 3 µm pore size Transwell™ filters (Corning) and all medium changes were accomplished through the filter membrane to protect the underlying mucus layer.

Growth medium was removed and replaced with 750 µl of fresh medium and 250 µl of either an oligouronate (G-block having a degree of polymerisation DP=20) or saline (control). 40 µl of Microbeads (FluoSpheres® carboxylate-modified microspheres, 0.02 µm, yellow-green fluorescent; Invitrogen) were added to test wells as a 0.02% suspension.

Incubation was performed at 37° C. for 2 hours and stopped by washing cells (×2) in cold PBS (2 ml). Cold trypsin/EDTA used to detach cells (2 ml), medium was added (2 ml) and the cells were spun down. Cells were washed (×2) in cold PBS (2 ml) and suspended in PBS (0.5 ml).

Flow cytometry was performed with fluorophore excitation using the 488 nm line of an argon laser with detectors optimised for the fluorophore.

Figure 1A:
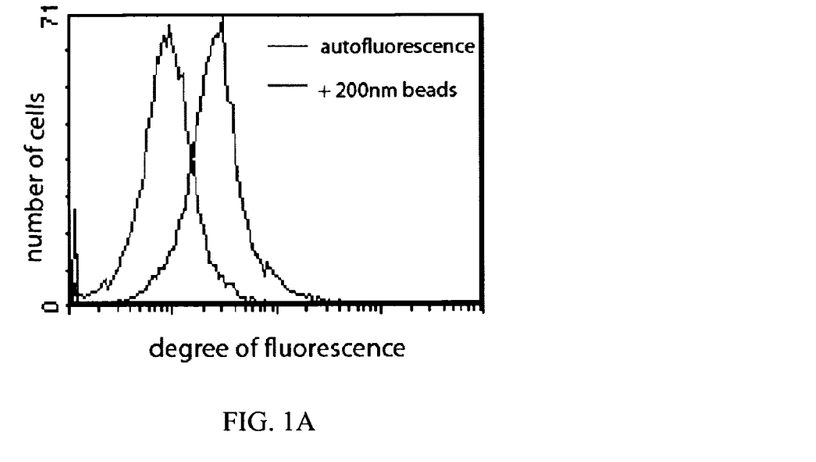
FIGS. 1A-1C show cellular uptake of microbeads in mucus-secreting cells.
Figure 1B:
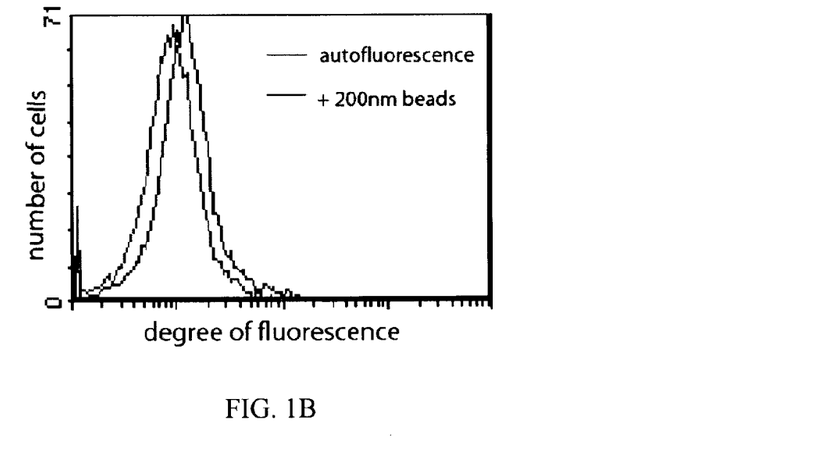
Figure 1C:
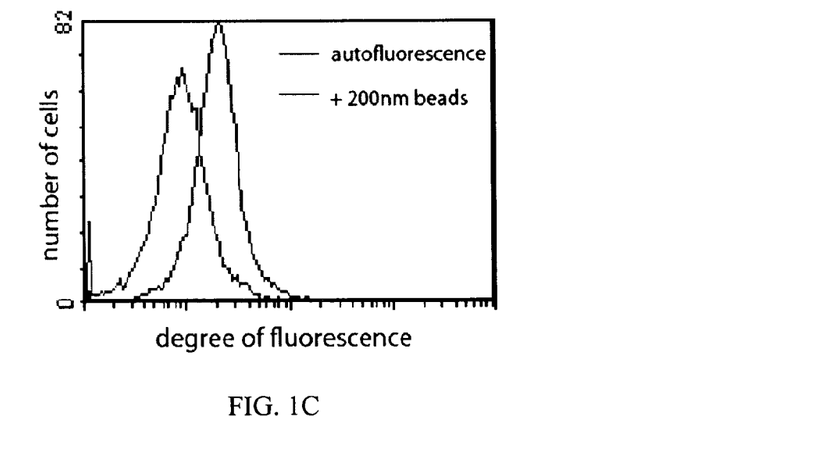

Results of this experiment are shown in FIGS. 1A, 1B and 1C. FIGS. 1A and 1B show that a continuous mucus layer is a barrier to cellular uptake of microbeads. FIG. 1C shows that addition of an oligouronate significantly increases uptake of microbeads in cells with a continuous mucus layer.

EXAMPLE 3

Effect of Oligouronate on Cellular Uptake of a siRNA Lipoplex

HeLa or HEK cells (commercially available) were grown to confluence in 6 well plates using OptiMEM® growth medium (Invitrogen).

The growth medium was removed and replaced with 750 µl of fresh medium and 250 µl of either an oligouronate (G-block having a degree of polymerisation DP=20) or saline (control).

Fluorescent siRNA/Lipofectamine™ RNAimax lipoplexes (Invitrogen) were then added to test wells according to the manufacturers recommended protocol and incubated at 37° C. for 2 hours. No transfection reagent was added to control wells.

Incubation was stopped by washing cells (×2) in cold PBS (2 ml). Cold trypsin/EDTA was used to detach cells (2 ml), medium was added (2 ml) and the cells were spun down and washed (×2) in cold PBS (2 ml). Cells were then suspended in PBS (0.5 ml).

Flow cytometry was performed with fluorophore excitation using the 488 nm line of an argon laser with detectors optimised for the fluorophore.

Figure 2A:
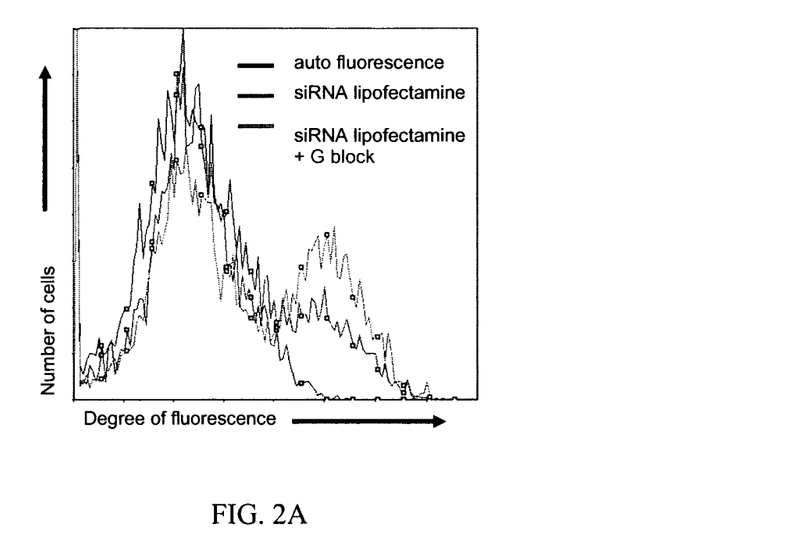
FIGS. 2A-2B show the effects of oligouronate on transfection of HEK and HeLa cells.
Figure 2B:
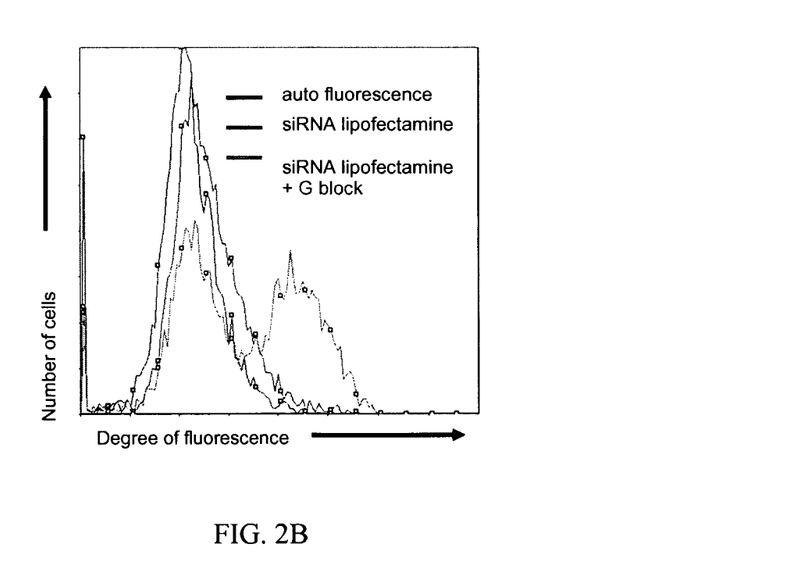

Results of this experiment are shown in FIGS. 2A and 2B. FIG. 2A shows the effect of oligouronate on transfection of HEK cells—some uptake of nucleic acid is seen without oligouronate, but greater uptake is observed when oligouronate is present. FIG. 2B shows the effect of oligouronate on transfection of HeLa cells—no uptake of nucleic acids is observed in the absence of oligouronate, however significant uptake is observed when the oligouronate is present.

EXAMPLE 4

Effect of Oligouronate on Cellular Uptake of Transferrin

MDCK or HeLa cells (commercially available) were grown to confluence in 6-well plates using OptiMEM® growth Medium (Invitrogen).

The growth medium was removed and replaced with 750 µl of fresh medium and 250 µl of either an oligouronate (G-block having a degree of polymerisation DP=20) or saline (control).

Cells were pre-incubated at 37° C. for 2 hours and then wells were washed (MDCK cells for washed samples only) twice with PBS.

5 µg or 10 µg of Alexa Fluor® 488-labelled transferrin (Invitrogen) was added to test wells. Wells without transferrin were used as auto fluorescence controls. The cells were then incubated at 37° C. for 2 hours.

The incubation was stopped by washing cells (×2) in cold PBS (2 ml). Cold trypsin/EDTA was used to detach cells (2 ml), medium was added (2 ml) and the cells were spun down. Cells were then washed (×2) in cold PBS (2 ml) and suspended in PBS (0.5 ml).

Flow cytometry was performed with fluorophore excitation using the 488 nm line of an argon laser with detectors optimised for the fluorophore. Results are shown in FIGS. 3-6.

Figure 3A:
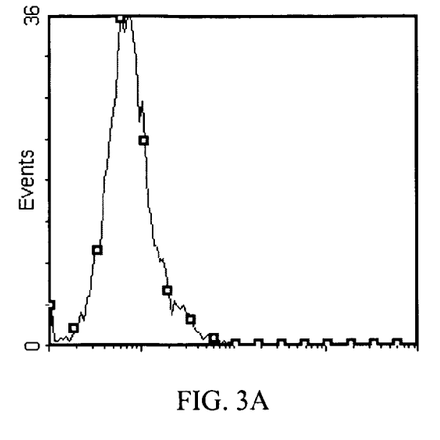
FIGS. 3A-3C show uptake of labelled transferrin into MDCK cells.
Figure 3B:
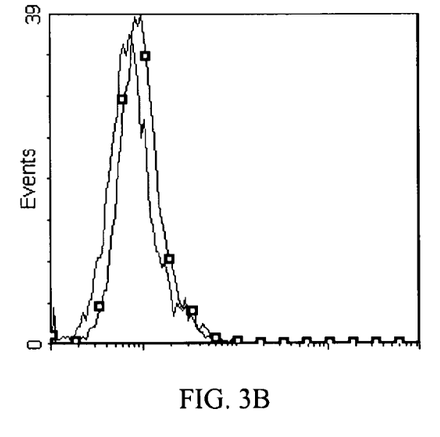
Figure 3C:
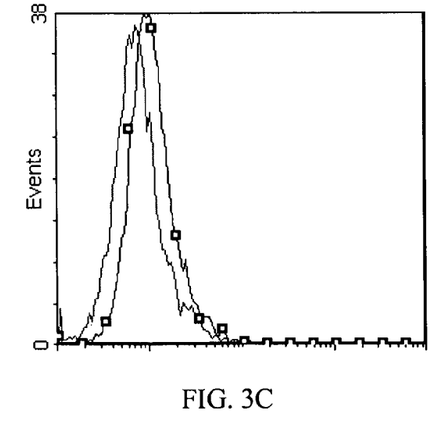
Figure 4A:
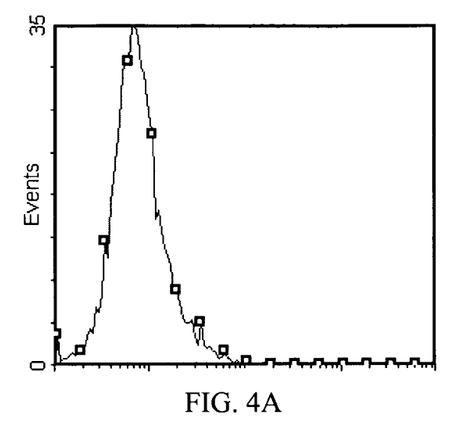
FIGS. 4A-4C show uptake of labelled transferrin into MDCK cells treated with oligouronate.
Figure 4B:
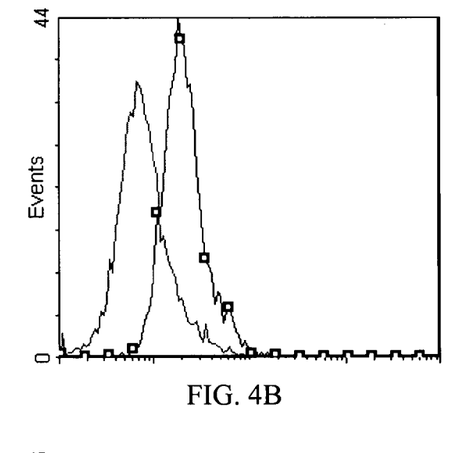
Figure 4C:
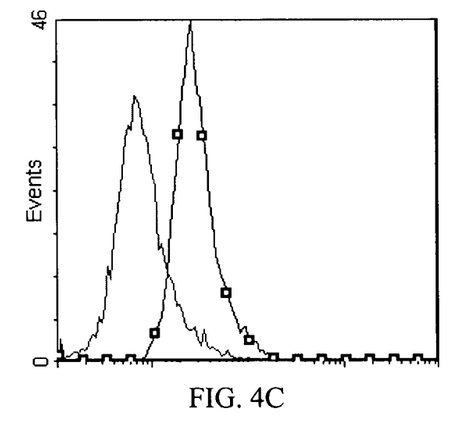
Figure 5A:
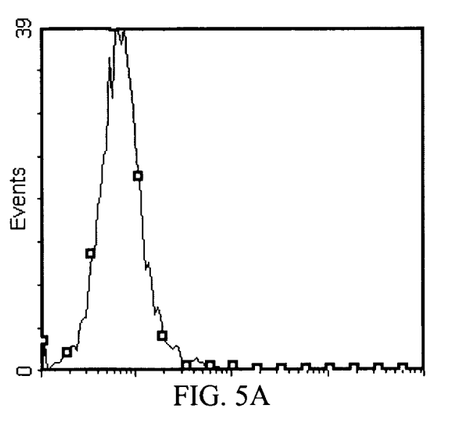
FIGS. 5A-5C show uptake of labelled transferrin into MDCK cells treated with oligouronate which is subsequently washed off.
Figure 5B:
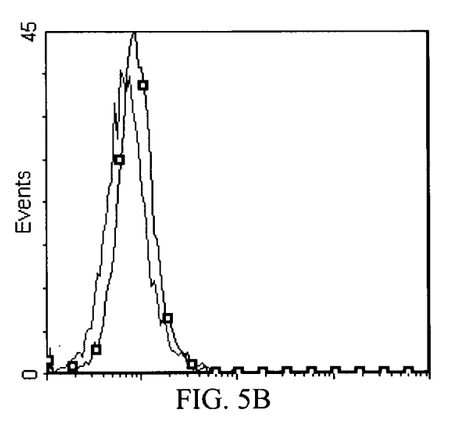
Figure 5C:
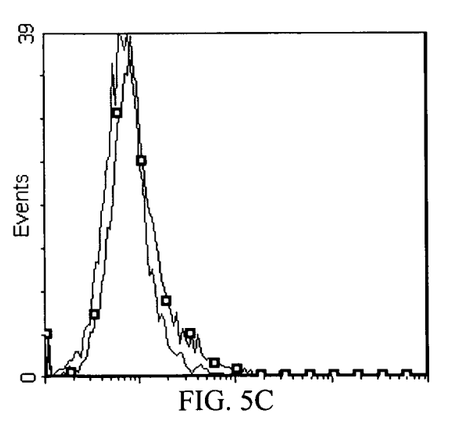

FIGS. 3A-3C show the results of flow cytometry of MDCK cells treated with the saline control (i.e. without oligouronate). FIGS. 4A-4C show the results of flow cytometry of MDCK cells treated with oligouronate. FIGS. 5A-5C show the results of flow cytometry of MDCK cells treated with oligouronate with the washing step included as described above. In each case, Figure A is the non-transferrin control curve; Figure B is an overlay of the control curve and the 5 µg transferrin sample curve; and Figure C is an overlay of the control curve and the 10 µg transferrin sample curve.

Figure 6:
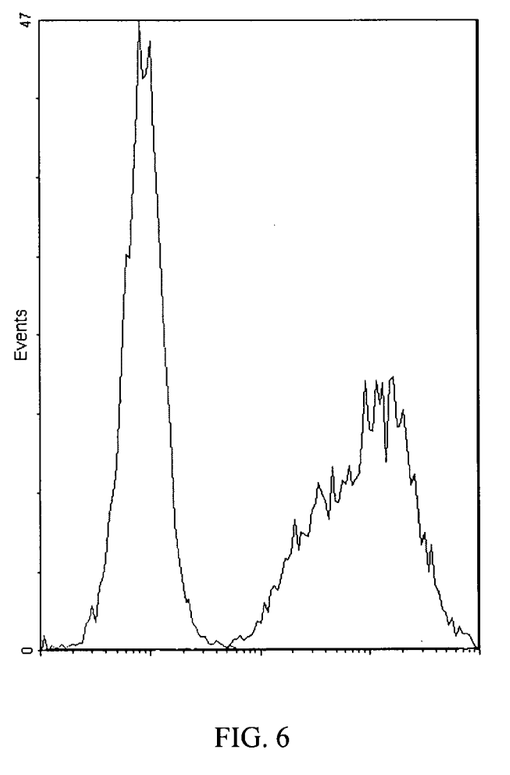
FIG. 6 shows uptake of labelled transferrin into HeLa cells with and without oligouronate treatment.

FIG. 6 shows the results of flow cytometry of HeLa cells treated. This figure is an overlay of the non-transferrin control curve (left-hand peak), the 5 µg transferrin sample curve without oligouronate treatment (light grey central peak), and the 5 µg transferrin sample curve with oligouronate treatment (dark grey right-hand peak).

From these data it can clearly be seen that treatment with oligouronate improved uptake of transferrin (FIGS. 4A, 4B and 6). Concurrent administration improved uptake (FIG. 4), but pre-treatment with oligouronate followed by washing of cells did not increase uptake of subsequently-administered transferrin (FIG. 5).

EXAMPLE 5

Mobility of Microbeads in Small Intestinal Mucus

Pig small intestinal mucus was scraped from mucosa of recently slaughtered pigs and frozen until use. Before use, the frozen mucus was defrosted over 24 hours at 4° C.

The microbeads used were FluoSpheres® carboxylate-modified, yellow-green fluorescent microspheres (Invitrogen) of 0.1, 0.2 and 0.5 µm diameter.

5.1 Experiments Using 0.1 and 0.5 µm Diameter Microbeads:

Control samples were prepared by adding 32 µl 0.05M NaCl solution to 260 µg small intestinal mucus (prepared as described above), stirred well for 1 hour and allowed to equilibrate for 1 hour. 8 µl microbeads (2% suspension) were vortexed and then added to the mucus preparation. The mixture was stirred well for 1 hour and allowed to equilibrate overnight at 4° C.

Samples including oligouronate were prepared as for the control sample, except that 32 µl 40 mg/ml oligouronate (G-block having a degree of polymerisation DP=20) in 0.05M NaCl was used in place of the 0.05M NaCl solution.

Samples were used to fill confocal imaging chambers.

A region of interest was then bleached using the 488 nm line of an argon laser at full power and fluorescence recovery after photobleaching (FRAP) by diffusion was monitored at 2% laser power 5.2 Experiments Using 0.2 µm Diameter Microbeads:

Mucin (prepared as described above) was solubilised in 50 mM NaCl at a concentration of 25 mg/ml. Oligouronate (G-block having a degree of polymerisation DP=20) was solubilised in 50 mM NaCl at a concentration of 30 mg/ml Microbeads sample (without mucin)

16 µl microbead suspension was vortexed and added to 384 µl 50 mM NaCl.

Final concentration $1.8 \times 10^{11}$ beads/ml

Mucin sample (without oligouronate)

16 µl microbead suspension was vortexed and added to 64 µl 50 mM NaCl and 320 µl mucin solution.

Final concentration $1.8 \times 10^{11}$ beads/ml, 20 mg/ml mucin

Mucin and oligouronate sample

16 µl microbead suspension was vortexed and added to 64 µl oligouronate solution. 320 µl mucin solution was then added.

Final concentration $1.8 \times 10^{11}$ beads/ml, 20 mg/ml mucin, 4.8 mg/ml oligouronate.

Samples were used to fill confocal imaging chambers.

Figure 7:
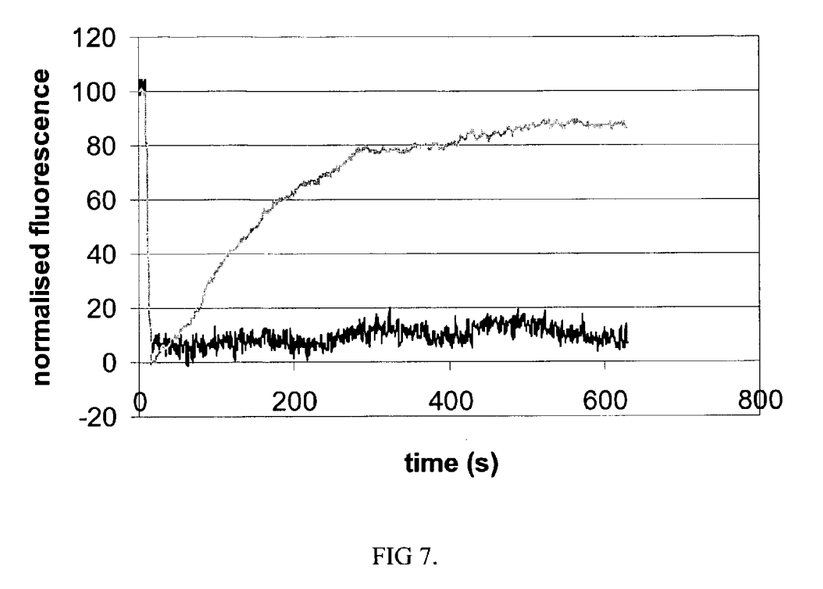
FIG. 7 shows diffusion of 0.5 µm microbeads into mucus after photobleaching.
Figure 8:
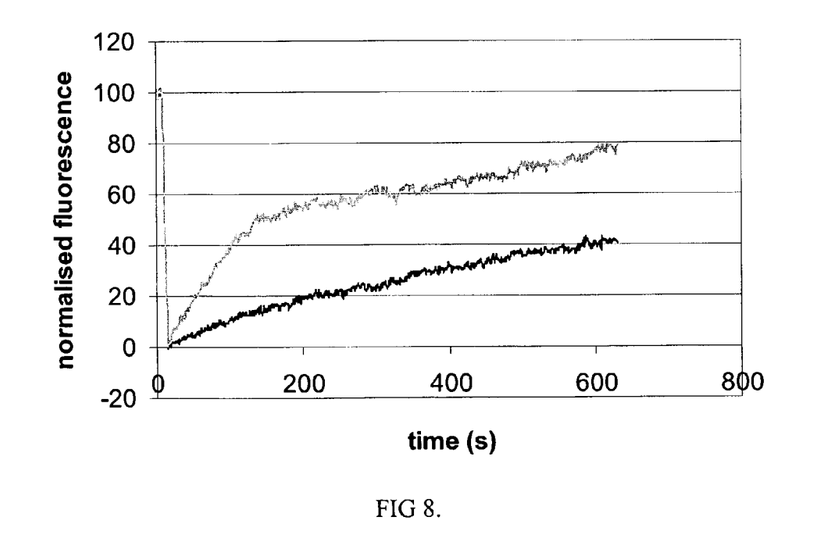
FIG. 8 shows diffusion of 0.1 µm microbeads into mucus after photobleaching.
Figure 9:
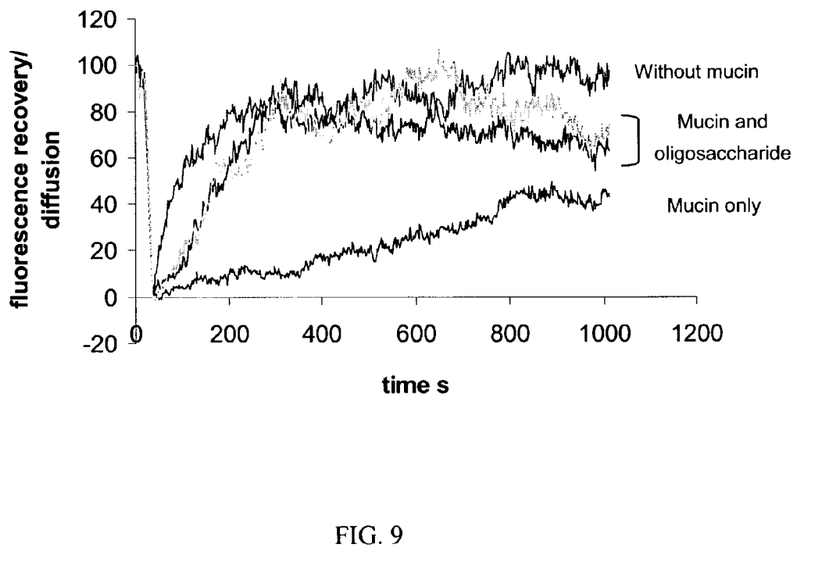
FIG. 9 shows diffusion of 0.2 µm microbeads into mucus after photobleaching.

A region of interest was then bleached using the 488 nm line of an argon laser at full power and FRAP by diffusion was monitored at 5% laser power 5.3 Results:

Results are shown in FIGS. 7, 8 and 9.

FIG. 7 shows the FRAP of 0.5 µm microbeads in small intestinal mucus. The black lower line is the control sample (without oligouronate) and the grey upper line shows recovery of fluorescence in the sample treated with oligouronate.

FIG. 8 shows the FRAP of 0.1 µm microbeads in small intestinal mucus. The black lower line is the control sample (without oligouronate) and the grey upper line shows recovery of fluorescence in the sample treated with oligouronate.

FIG. 9 shows the FRAP of 0.2 µm microbeads in small intestinal mucus. The black lower line is the control sample (without oligouronate), the dark grey upper line shows FRAP of the sample without mucin, and the two inner lines (dark and light) show recovery of fluorescence in mucin samples treated with oligouronate.

These data indicate that small intestinal mucus is a significant barrier to the diffusion of particles having sub-micron dimensions. Addition of oligouronate significantly reduces the diffusion barrier posed by mucus.

EXAMPLE 6

Scanning Electron Microscopy (SEM) of Gastric Mucin

Mucin (pig gastric mucin prepared as described above) was solubilised in 50 mM NaCl at a concentration of 25 mg/ml and 30 mg/ml.

Oligouronate (as described in Example 5) was solubilised in 50 mM NaCl at a concentration of 30 mg/ml.

SEM samples were prepared as follows:

Mucin (25 mg/ml)

336 µl 30 mg/ml mucin was added to 64 µl 0.05M NaCl and mixed.

Mucin (20 mg/ml)

320 µl 25 mg/ml mucin was added to 80 µl 0.05M NaCl and mixed.

Mucin (25 mg/ml)+oligouronate

336 µl 30 mg/ml mucin added to 64 µl oligouronate in 0.05M NaCl and mixed.

Mucin (20 mg/ml)+oligouronate

320 µl 30 mg/ml mucin was added to 640 G-block in 0.05M NaCl and 16 µl 0.05M NaCl and mixed.

Samples were dehydrated in graduated acetone/water, dried using critical point drying and visualised by scanning electron microscopy.

Results are shown in FIGS. 10-13.

Figure 10:
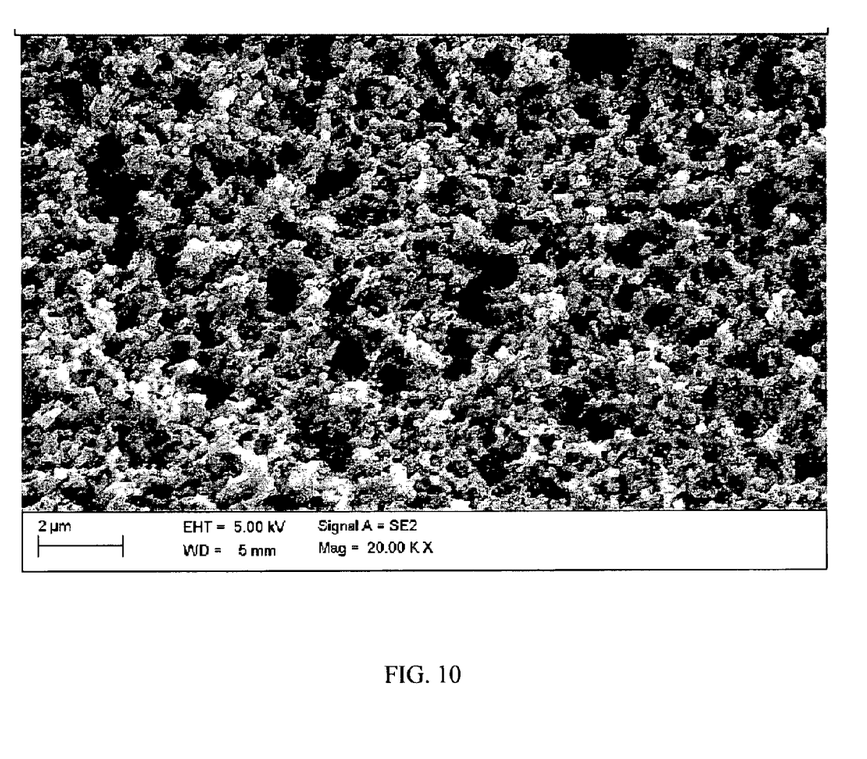
FIGS. 10-13 are scanning electron micrographs of pig gastric mucin at 20 and 25 mg/ml concentrations, with and without oligouronate treatment.
Figure 11:
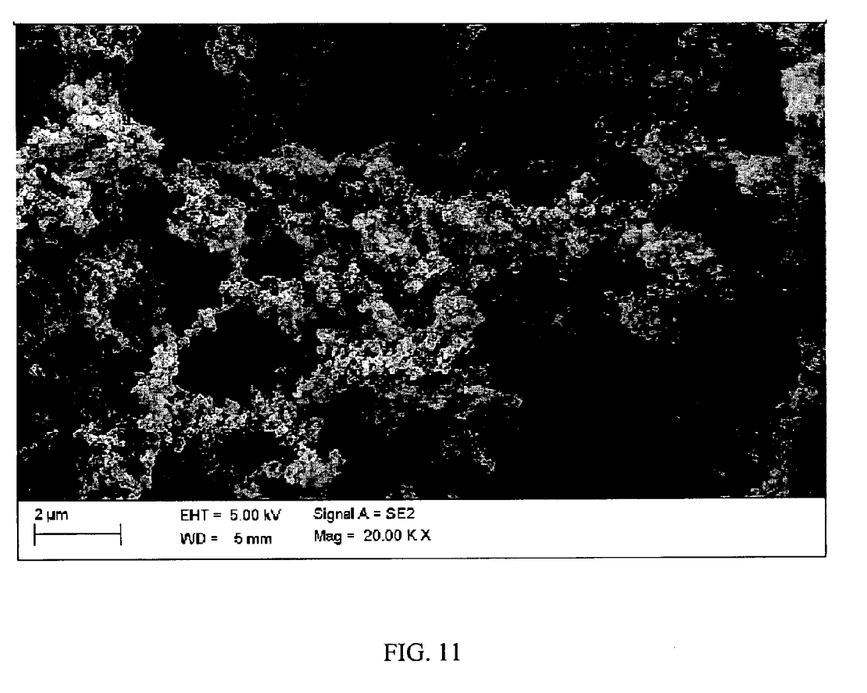
Figure 12:
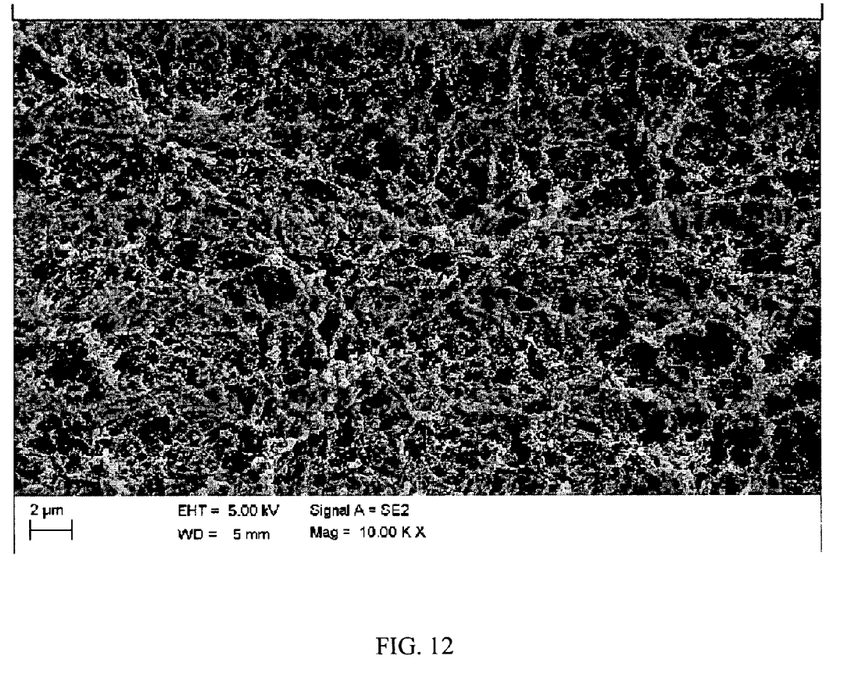
Figure 13:
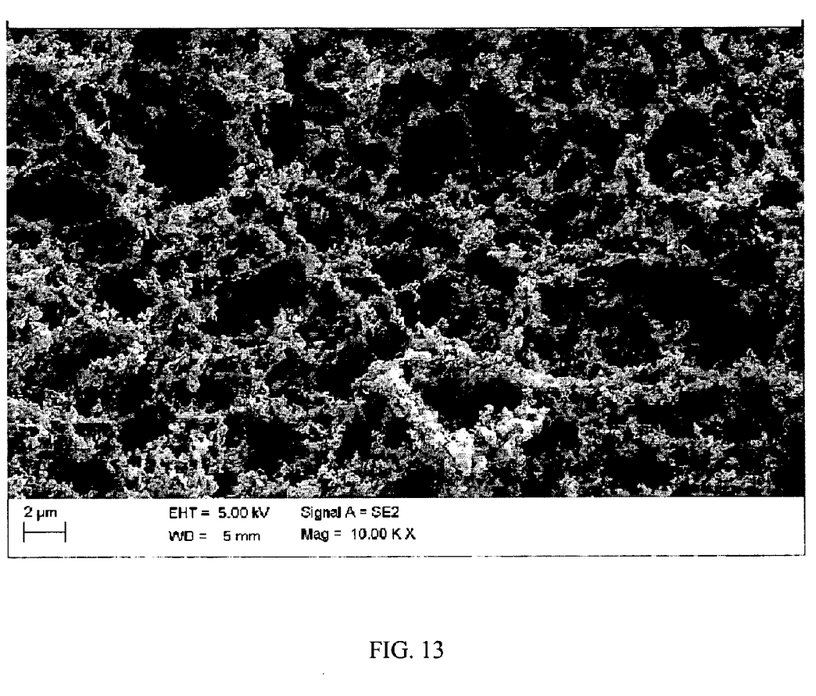

FIGS. 10 and 11 show the structure of the 20 mg/ml mucin samples without and with 4.8 mg/ml oligouronate, respectively. FIGS. 12 and 13 show the structure of the 25 mg/ml mucin samples without and with 4.8 mg/ml oligouronate, respectively.

These data indicate that addition of oligouronate to gastric mucus results in an opening of the network structure of the mucin matrix and an increase in pore size.

The invention claimed is:

1. An oral pharmaceutical composition comprising an enteric-coated drug substance, wherein said composition also comprises an enteric-coated oligouronate and wherein said drug substance is a peptide or peptide derivative.

2. A composition as claimed in claim 1 wherein said drug substance is an oligopeptide or a polypeptide.

3. A composition as claimed in claim 1 wherein said drug substance is insulin.

4. A composition as claimed in claim 1 wherein said drug substance is an antigenic fragment from a parasitic or infective species, optionally conjugated to an immunogenic carrier.

5. A composition as claimed in claim 1 in coated tablet or capsule form.

6. A method of treating a human or non-human subject comprising orally administering to said subject an effective dose of a composition according to claim 1, wherein a condition in said subject is responsive to said drug substance in said composition.

7. A method of treating a human or non-human subject comprising orally administering to said subject an effective dose of an enteric-coated drug substance, wherein the drug substance is simultaneously, sequentially or separately administered with the enteric-coated oligouronate and wherein said drug substance is a peptide or peptide derivative.

8. The method of claim 6, wherein the condition to be treated is selected from the group consisting of diabetes, cancer, cardiovascular disease and Gaucher's disease.

9. The method of claim 7 wherein said drug substance is an oligopeptide or a polypeptide.

10. The method of claim 7 wherein said drug substance is insulin.

11. The method of claim 7 wherein said drug substance is an antigenic fragment from a parasitic or infective species, optionally conjugated to an immunogenic carrier.

* * * * *